United States Patent
Yang et al.

(10) Patent No.: US 10,544,409 B2
(45) Date of Patent: *Jan. 28, 2020

(54) HEXURONATE C4-EPIMERASE MUTANT WITH IMPROVED CONVERSION ACTIVITY, AND METHOD FOR PRODUCING D-TAGATOSE BY USING SAME

(71) Applicant: CJ CHEILJEDANG CORPORATION, Seoul (KR)

(72) Inventors: Sung Jae Yang, Suwon-si (KR); Yang Hee Kim, Suwon-si (KR); Il Hyang Park, Suwon-si (KR); Young Mi Lee, Suwon-si (KR); Hyun Kug Cho, Seoul (KR); Seong Bo Kim, Seongnam-si (KR); Seung Won Park, Yongin-si (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/231,239

(22) Filed: Dec. 21, 2018

(65) Prior Publication Data

US 2019/0136223 A1 May 9, 2019

Related U.S. Application Data

(63) Continuation of application No. 15/748,164, filed as application No. PCT/KR2016/008412 on Jul. 29, 2016, now Pat. No. 10,196,626.

(30) Foreign Application Priority Data

Jul. 29, 2015 (KR) .................. 10-2015-0107436

(51) Int. Cl.
| | | |
|---|---|---|
| *C12P 19/24* | (2006.01) | |
| *C12N 9/90* | (2006.01) | |
| *C12P 19/02* | (2006.01) | |
| *C12N 1/20* | (2006.01) | |
| *C12R 1/19* | (2006.01) | |

(52) U.S. Cl.
CPC .................. *C12N 9/90* (2013.01); *C12N 1/20* (2013.01); *C12P 19/02* (2013.01); *C12P 19/24* (2013.01); *C12Y 501/02* (2013.01); *C12R 1/19* (2013.01)

(58) Field of Classification Search
CPC .................................. C12P 19/02; C12N 9/90
USPC ........................................................... 435/94
See application file for complete search history.

(56) References Cited

U.S. PATENT DOCUMENTS 10,196,626 B2 * 2/2019 Yang .................. C12P 19/02

FOREIGN PATENT DOCUMENTS

| KR | 10-2002-0050067 A | 6/2002 |
|---|---|---|
| KR | 10-2009-0082774 A | 7/2009 |
| KR | 10-2014-0111093 A | 9/2014 |
| KR | 10-2014-0143109 A | 12/2014 |

OTHER PUBLICATIONS

NCBI References Sequence No. WP_015918744.1—2 pages (May 21, 2013).
Rodionova et al., "Tagaturonate-fructuronate-epimerase Uxa E, a novel enzyme in the hexuronate catabolic network in Tehmotoga martimia", Envorinmental Microbiology,vol. 14, No. 11—16 pages(2012).
International Search Report of corresponding Patent Application No. PCT/KR2016/008412—4 pages (Oct. 20, 2016).

* cited by examiner

*Primary Examiner* — Tekchand Saidha
(74) *Attorney, Agent, or Firm* — Knobbe Martens Olson & Bear LLP

(57) ABSTRACT

A hexuronate C4-epimerase with improved conversion activity and a method for producing D-tagatose using the hexuronate C4-epimerase. The hexuronate C4-epimerase includes an amino acid sequence set forth in SEQ ID NO: 1, in which serine (S) at position 125, serine (S) at position 185, valine (V) at position 267, serine (S) at position 268, threonine (T) at position 272, tryptophan (W) at position 306, arginine (R) at position 386 and tyrosine (Y) at position 403 from an N-terminal of hexunorate C4-epimerase are mutated.

20 Claims, No Drawings

Specification includes a Sequence Listing.

HEXURONATE C4-EPIMERASE MUTANT WITH IMPROVED CONVERSION ACTIVITY, AND METHOD FOR PRODUCING D-TAGATOSE BY USING SAME

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 29777067_1, the date of creation of the ASCII text file is Jan. 18, 2019, and the size of the ASCII text file is 12.9 KB.

TECHNICAL FIELD

The present invention relates to a hexuronate C4-epimerase variant with improved conversion activity and a method for producing D-tagatose using the same.

BACKGROUND

Tagatose is a natural sweetener present only in small amounts in foods such as milk, cheese, cacao, and the like and in naturally sweet fruits such as apples, mandarins, and the like, and has physical properties similar to sucrose. Tagatose has a low-calorie value of 1.5 kcal/g corresponding to one-third that of sucrose and glycemic index (GI) of 3 corresponding to 5% that of sucrose. Tagatose has a sweet taste similar to sucrose and has various health and functional characteristics, and thus has been used in various products as an alternative sweetener capable of satisfying both taste and health.

Tagatose can be produced from galactose, as a raw material, by a chemical isomerization (catalytic reaction) method and a biological (enzymatic isomerization reaction) method (see Korean Patent Publication No. 2009-0082774 A). However, the price of lactose, which is a raw material for tagatose, is unstable depending on produced amounts, supply of and demand for raw milk and lactose on the global market, and the like, and such a price fluctuation in raw milk makes stable supply of raw materials for tagatose production difficult. Therefore, there is a need for a new method for producing tagatose using general saccharides (sucrose, glucose, fructose, and the like).

SUMMARY

It is one object of the present invention to provide a hexuronate C4-epimerase variant with improved conversion activity. In accordance with one embodiment of the present invention, there is provided a hexuronate C4-epimerase variant having an amino acid sequence set forth in SEQ ID NO: 1 wherein serine (S) at position 125, serine (S) at position 185, valine (v) at position 267, serine (S) at position 268, threonine (T) at position 272, tryptophan (W) at position 306 and arginine (R) at position 386 and tyrosine (Y) at position 403 from the N-terminal of the hexunorate C4-epimerase are mutated.

It is another object of the present invention to provide a nucleic acid encoding the hexuronate C4-epimerase variant, a transformant including the nucleic acid, or a composition for producing D-tagatose including the hexuronate C4-epimerase variant according to the present invention.

It is a further object of the present invention to provide a method for producing D-tagatose, including: contacting and epimerizing D-fructose with the hexuronate C4-epimerase variant, the transformant, or the composition for producing D-tagatose according to the present invention.

Hereinafter, embodiments of the present invention will be described in more detail. Descriptions of details apparent to those skilled in the art will be omitted herein.

In order to accomplish the above and other objects of the present invention, one aspect of the present invention provides a hexuronate C4-epimerase variant having an amino acid sequence set forth in SEQ ID NO: 1 in which at least one amino acid selected from the group consisting of histidine (H) at position 9, tyrosine (Y) at position 21, glutamic acid (E) at position 60, valine (V) at position 62, glutamic acid (E) at position 68, leucine (L) at position 77, leucine (L) at position 91, threonine (T) at position 97, serine (S) at position 125, valine (V) at position 126, leucine (L) at position 140, aspartic acid (D) at position 141, tryptophan (W) at position 145, glutamine (Q) at position 149, glycine (G) at position 157, alanine (A) at position 158, alanine (A) at position 160, valine (V) at position 163, lysine (K) at position 164, proline (P) at position 166, glutamic acid (E) at position 167, aspartic acid (D) at position 168, glutamic acid (E) at position 175, glycine (G) at position 176, phenylalanine (F) at position 177, serine (S) at position 185, methionine (M) at position 202, glycine (G) at position 218, tyrosine (Y) at position 221, aspartic acid (D) at position 231, valine (V) at position 241, tyrosine (Y) at position 242, valine (V) at position 267, serine (S) at position 268, threonine (T) at position 272, threonine (T) at position 276, valine (V) at position 284, phenylalanine (F) at position 295, phenylalanine (F) at position 297, phenylalanine (F) at position 302, tryptophan (W) at position 306, leucine (L) at position 316, lysine (K) at position 337, proline (P) at position 351, phenylalanine (F) at position 361, alanine (A) at position 366, arginine (R) at position 386, isoleucine (I) at position 388, serine (S) at position 402, tyrosine (Y) at position 403, valine (V) at position 415, aspartic acid (D) at position 429, tyrosine (Y) at position 440 and glycine (G) at position 441 from the N-terminal of the hexuronate C4-epimerase is mutated into another amino acid [see Tables 2 to 5 below].

According to one embodiment of the present invention, the hexuronate C4-epimerase variant may be a hexuronate C4-epimerase variant in which tyrosine (Y) at position 403 from the N-terminal of the hexuronate C4-epimerase having an amino acid sequence set forth in SEQ ID NO: 1 is mutated.

Tyrosine (Y) at position 403 of the hexuronate C4-epimerase variant may be substituted with alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), or tryptophan (W).

In one embodiment, the hexuronate C4-epimerase variant may be further mutated at serine at position 125 in addition to position 403.

Serine (S) at position 125 of the hexuronate C4-epimerase variant may be substituted with aspartic acid (D), glutamine (Q), glutamic acid (E), threonine (T), asparagine (N), cysteine (C), or tyrosine (Y).

In one embodiment, the hexuronate C4-epimerase variant may be further mutated at one or more amino acid residues selected from the group consisting of serine (S) at position 185, valine (V) at position 267, serine (S) at position 268, threonine (T) at position 272, tryptophan (W) at position 306, and arginine (R) at position 386, in addition to tyrosine (Y) at position 403 and serine (S) at position 125.

Serine (S) at position 185 of the hexuronate C4-epimerase variant may be substituted with lysine (K), arginine (R), histidine (H), glutamine (Q), alanine (A), or glycine (G); valine (V) at position 267 may be substituted with methionine (M); serine (S) at position 268 may be substituted with cysteine (C), or threonine (T); threonine (T) at position 272 may be substituted with alanine (A), aspartic acid (D), glutamic acid (E), phenylalanine (F), glycine (G), histidine (H), isoleucine (I), lysine (K), leucine (L), methionine (M), glutamine (Q), arginine (R), serine (S), or valine (V); tryptophan (W) at position 306 may be substituted with phenylalanine (F), histidine (H), methionine (M), or valine (V); and arginine (R) at position 386 may be substituted with proline (P), or valine (V).

In one embodiment, the hexuronate C4-epimerase variant may be further mutated at serine (S) at position 268, in addition to tyrosine (Y) at position 403 and serine (S) at position 125. Here, the hexuronate C4-epimerase variant may be further mutated at lysine (K) at position 164, aspartic acid (D) at position 168, glutamic acid (E) at position 175, asparagine (N) at position 297 and isoleucine (I) at position 388. In the hexuronate C4-epimerase variant, lysine (K) at position 164 may be substituted with methionine, aspartic acid (D) at position 168 may be substituted with glutamic acid, glutamic acid (E) at position 175 may be substituted with glycine (G), asparagine (N) at position 297 may be substituted with lysine (K), and isoleucine (I) at position 388 may be substituted with valine (V).

In one embodiment, the hexuronate C4-epimerase variant may be further mutated at valine (V) at position 267 and arginine (R) at position 386, in addition to tyrosine (Y) at position 403 and serine (S) at position 125. Here, the hexuronate C4-epimerase variant may be further mutated at proline (P) at position 351. In the hexuronate C4-epimerase variant, proline (P) at position 351 may be substituted with serine (S).

In one embodiment, the hexuronate C4-epimerase variant may be further mutated at serine (S) at position 185, valine (V) at position 267 and tryptophan (W) at position 306, in addition to tyrosine (Y) at position 403 and serine (S) at position 125. Here, the hexuronate C4-epimerase variant may be further mutated at glutamic acid (E) at position 68. In the hexuronate C4-epimerase variant, glutamic acid (E) at position 68 may be substituted with glycine (G).

In one embodiment, the hexuronate C4-epimerase variant may be further mutated at valine (V) at position 267, serine (S) at position 268, and arginine (R) at position 386, in addition to tyrosine (Y) at position 403 and serine (S) at position 125. Here, the hexuronate C4-epimerase variant may be further mutated at glutamic acid (E) at position 60, methionine (M) at position 202, tyrosine (Y) at position 221, and tyrosine (Y) at position 242. In the hexuronate C4-epimerase variant, glutamic acid (E) at position 60 may be substituted with aspartic acid (D), methionine (M) at position 202 may be substituted with threonine, tyrosine (Y) at position 221 may be substituted with phenylalanine (F) and tyrosine (Y) at position 242 may be substituted with phenylalanine (F).

In one embodiment, the hexuronate C4-epimerase variant may be further mutated at one or more amino acid residues selected from the group consisting of serine (S) at position 185, valine (V) at position 267, serine (S) at position 268, and threonine (T) at position 272, in addition to tyrosine (Y) at position 403 and serine (S) at position 125. Here, the hexuronate C4-epimerase variant may be further mutated at one or more amino acid residues selected from the group consisting of leucine (L) at position 91, aspartic acid (D) at position 141 and glycine (G) at position 176. In the hexuronate C4-epimerase variant, leucine (L) at position 91 may be substituted with tryptophan (W), isoleucine (I), or asparagine (N); aspartic acid (D) at position 141 may be substituted with phenylalanine (F); and glycine (G) at position 176 may be substituted with histidine (H), phenylalanine (F), or tyrosine (Y).

In one embodiment, the hexuronate C4-epimerase variant may be further mutated at one or more amino acid residues selected from the group consisting of valine (V) at position 267, serine (S) at position 268, threonine (T) at position 272, and tryptophan (W) at position 306, in addition to tyrosine (Y) at position 403 and serine (S) at position 125. Here, the hexuronate C4-epimerase variant may be further mutated at valine (V) at position 284 and valine (V) at position 415. In the hexuronate C4-epimerase variant, valine (V) at position 284 may be substituted with alanine (A); and valine (V) at position 415 may be substituted with glutamic acid (E).

In one embodiment, the hexuronate C4-epimerase variant may be further mutated at one or more amino acid residues selected from the group consisting of serine (S) at position 185, valine (V) at position 267, serine (S) at position 268, threonine (T) at position 272, and tryptophan (W) at position 306, in addition to tyrosine (Y) at position 403 and serine (S) at position 125. Here, the hexuronate C4-epimerase variant may be further mutated at proline (P) at position 166 or aspartic acid (D) at position 231. In the hexuronate C4-epimerase variant, proline (P) at position 166 may be substituted with arginine (R); and aspartic acid (D) at position 231 may be substituted with arginine (R).

In one embodiment, the hexuronate C4-epimerase variant may be further mutated at serine (S) at position 185, valine (V) at position 267, serine (S) at position 268, threonine (T) at position 272, and tryptophan (W) at position 386, in addition to tyrosine (Y) at position 403 and serine (S) at position 125. Here, the hexuronate C4-epimerase variant may be further mutated at valine (V) at position 126. In the hexuronate C4-epimerase variant, valine (V) at position 126 may be substituted with alanine (A), phenylalanine (F), glycine (G), isoleucine (I), leucine (L), proline (P), asparagine (R), or threonine (T).

In one embodiment, the hexuronate C4-epimerase variant may be a hexuronate C4-epimerase variant having an amino acid sequence set forth in SEQ ID NO: 1 in which tyrosine (Y) at position 403, serine (S) at position 125, serine (S) at position 185, valine (v) at position 267, serine (S) at position 268, threonine (T) at position 272, tryptophan (W) at position 306, and arginine (R) at position 386 from the N-terminal of the hexunorate C4-epimerase are mutated.

In one embodiment, the hexuronate C4-epimerase variant may be further mutated at threonine (T) at position 97, valine (V) at position 126, tryptophan (W) at position 145, valine (V) at position 163, lysine (K) at position 164, proline (P) at position 166, aspartic acid (D) at position 231, valine (V) at position 241, threonine (T) at position 276, lysine (K)

at position 337, alanine (A) at position 366, serine (S) at position 402, aspartic acid (D) at position 429, or tyrosine (Y) at position 440, in addition to tyrosine (Y) at position 403, serine (S) at position 125, serine (S) at position 185, valine (v) at position 267, serine (S) at position 268, threonine (T) at position 272, and tryptophan (W) at position 386. In the hexuronate C4-epimerase variant, threonine (T) at position 97 may be substituted with alanine (A), or leucine (L); valine (V) at position 126 may be substituted with phenylalanine (F), leucine (L), proline (P), isoleucine (I), threonine (T), alanine (A), glycine (G), or arginine (R); tryptophan (W) at position 145 may be substituted with alanine (A); valine (V) at position 163 may be substituted with alanine (A), methionine (M), or glutamine (Q); lysine (K) at position 164 may be substituted with methionine (M); proline (P) at position 166 may be substituted with arginine (R); aspartic acid (D) at position 231 may be substituted with arginine (R); valine (V) at position 241 may be substituted with asparagine (N), threonine (T), or cysteine (S); threonine (T) at position 276 may be substituted with glutamic acid (E), or alanine (A); lysine (K) at position 337 may be substituted with glutamic acid (E), phenylalanine (F), asparagine (N), proline (P), serine (S), threonine (T), tryptophan (W), or tyrosine (Y); alanine (A) at position 366 may be substituted with serine (S), glycine (G), or cysteine (C); serine (S) at position 402 may be substituted with phenylalanine (F), cysteine (C), or tyrosine (Y); aspartic acid (D) at position 429 may be substituted with proline (P); and tyrosine (Y) at position 440 may be substituted with alanine (A).

In one embodiment, the hexuronate C4-epimerase variant may be further mutated at lysine (K) at position 164, aspartic acid (D) at position 166, or aspartic acid (D) at position 231, in addition to tyrosine (Y) at position 403, serine (S) at position 125, serine (S) at position 185, valine (V) at position 267, serine (S) at position 268, threonine (T) at position 272, and tryptophan (W) at position 386. In the hexuronate C4-epimerase variant, lysine (K) at position 164 may be substituted with methionine (M); aspartic acid (D) at position 166 may be substituted with arginine (R); and aspartic acid (D) at position 231 may be substituted with arginine (R).

In one embodiment, the hexuronate C4-epimerase variant may be further mutated at aspartic acid (D) at position 231, in addition to tyrosine (Y) at position 403, serine (S) at position 125, serine (S) at position 185, valine (V) at position 267, serine (S) at position 268, threonine (T) at position 272, tryptophan (W) at position 386, and valine (V) at position 163. In the hexuronate C4-epimerase variant, aspartic acid (D) at position 231 may be substituted with arginine (R).

In one embodiment, the hexuronate C4-epimerase variant may be further mutated at glycine (G) at position 157, alanine (A) at position 160, glutamic acid (E) at position 167, phenylalanine (F) at position 177, glycine (G) at position 218, phenylalanine (F) at position 295, phenylalanine (F) at position 302, phenylalanine (F) at position 361, alanine (A) at position 366, or glycine (G) at position 441, in addition to tyrosine (Y) at position 403, serine (S) at position 125, serine (S) at position 185, valine (V) at position 267, serine (S) at position 268, threonine (T) at position 272, tryptophan (W) at position 386 and lysine (K) at position 337. In the hexuronate C4-epimerase variant, glycine (G) at position 157 may be substituted with arginine (R); alanine (A) at position 160 may be substituted with leucine (L), phenylalanine (F), arginine (R), or tyrosine (Y); glutamic acid (E) at position 167 may be substituted with alanine (A), tryptophan (W), isoleucine (I), lysine (K), methionine (M), valine (V), or serine (S); phenylalanine (F) at position 177 may be substituted with tyrosine (Y), histidine (H), or leucine (L); glycine (G) at position 218 may be substituted with isoleucine (I), serine (S), leucine (L), phenylalanine (F), or cysteine (C); phenylalanine (F) at position 295 may be substituted with cysteine (C), arginine (R), or tyrosine (Y); phenylalanine (F) at position 302 may be substituted with cysteine (C); phenylalanine (F) at position 361 may be substituted with lysine (K), glutamic acid (E), valine (V), tryptophan (W), tyrosine (Y), methionine (M), arginine (R), glutamine (Q), leucine (L), or cysteine (C); alanine (A) at position 366 may be substituted with serine (S); and glycine (G) at position 441 may be substituted with glutamic acid (E), tryptophan (W), histidine (H), lysine (K), alanine (A), arginine (R), serine (S), or phenylalanine (F).

In one embodiment, the hexuronate C4-epimerase variant may be further mutated at leucine (L) at position 77, alanine (A) at position 158, or a combination thereof, in addition to tyrosine (Y) at position 403 and serine (S) at position 125. In the hexuronate C4-epimerase variant, leucine (L) at position 77 may be substituted with proline (P), or arginine (R); and alanine (A) at position 158 may be substituted with threonine (T). The hexuronate C4-epimerase variant in which tyrosine (Y) at position 403, serine (S) at position 125, leucine (L) at position 77 and alanine (A) at position 158 are mutated may be further mutated at arginine (R) at position 386. In the hexuronate C4-epimerase variant, arginine (R) at position 386 may be substituted with proline (P), or valine (V).

According to one embodiment of the present invention, the hexuronate C4-epimerase variant may be a hexuronate C4-epimerase variant in which serine (S) at position 185 from the N-terminal of the hexuronate C4-epimerase having an amino acid sequence set forth in SEQ ID NO: 1 is mutated. In one embodiment, the hexuronate C4-epimerase variant may be further mutated at serine (S) at position 125, in addition to position 185.

In one embodiment, the hexuronate C4-epimerase variant may be further mutated at serine (S) at position 268, threonine (T) at position 272 or a combination thereof, in addition to serine (S) at position 185 and serine (S) at position 125. Here, the hexuronate C4-epimerase variant may be further mutated at valine (V) at position 267, tryptophan (W) at position 306 or a combination thereof. In one embodiment, the hexuronate C4-epimerase variant in which serine (S) at position 185, serine (S) at position 125, serine (S) at position 268, threonine (T) at position 272, valine (V) at position 267 and tryptophan (W) at position 306 are mutated may be further mutated at arginine (R) at position 386.

According to one embodiment of the present invention, the hexuronate C4-epimerase variant may be a hexuronate C4-epimerase variant in which threonine (T) at position 272 from the N-terminal of the hexuronate C4-epimerase having an amino acid sequence set forth in SEQ ID NO: 1 is mutated.

In one embodiment, the hexuronate C4-epimerase variant may be further mutated at serine (S) at position 125, valine (V) at position 267 and serine (S) at position 268, in addition to threonine (T) at position 272. Here, the hexuronate C4-epimerase variant may be further mutated at aspartic acid (D) at position 231 or arginine (R) at position 386. In the hexuronate C4-epimerase variant, aspartic acid (D) at position 231 may be substituted with arginine (R); and arginine (R) at position 386 may be substituted with proline (P), or valine (V).

In one embodiment, the hexuronate C4-epimerase variant may be further mutated at one or more amino acid residues selected from the group consisting of threonine (T) at position 97, glutamine (Q) at position 149, proline (P) at position 166 and proline (P) at position 351, in addition to threonine (T) at position 272, serine (S) at position 125, serine (S) at position 185, valine (V) at position 267, serine (S) at position 268 and arginine (R) at position 386. In the hexuronate C4-epimerase variant, threonine (T) at position 97 may be substituted with alanine (A), or leucine (L); glutamine (Q) at position 149 may be substituted with arginine (R); proline (P) at position 166 may be substituted with arginine (R); and proline (P) at position 351 may be substituted with serine (S).

In one embodiment, the hexuronate C4-epimerase variant may be further mutated at one or more amino acid residues selected from the group consisting of lysine (K) at position 164, aspartic acid (D) at position 168 and glutamic acid (E) at position 175, in addition to threonine (T) at position 272, serine (S) at position 125, valine (V) at position 267 and serine (S) at position 268. In the hexuronate C4-epimerase variant, lysine (K) at position 164 may be substituted with methionine (M); aspartic acid (D) at position 168 may be substituted with glutamic acid (E); and glutamic acid (E) at position 175 may be substituted with glycine (G).

According to one embodiment of the present invention, the hexuronate C4-epimerase variant may be a hexuronate C4-epimerase variant in which leucine (L) at position 77 from the N-terminal of the hexuronate C4-epimerase having an amino acid sequence set forth in SEQ ID NO: 1 is mutated.

In one embodiment, the hexuronate C4-epimerase variant may be further mutated at serine (S) at position 125, in addition to leucine (L) at position 77.

In one embodiment, the hexuronate C4-epimerase variant may be further mutated at one or more amino acid residues selected from the group consisting of alanine (A) at position 158 or proline (P) at position 351, in addition to leucine (L). In the hexuronate C4-epimerase variant, alanine (A) at position 158 may be substituted with threonine (T); and proline (P) at position 351 may be substituted with serine (S). The hexuronate C4-epimerase variant may be further mutated at one or more amino acid residues selected from the group consisting of histidine at position 9, glutamic acid (E) at position 60, and valine (V) at position 415, in addition to leucine (L) at position 77, serine (S) at position 125 and 158 alanine (A). In the hexuronate C4-epimerase variant, histidine at position 9 may be substituted with tyrosine (Y), glutamic acid (E) at position 60 may be substituted with aspartic acid (D), and valine (V) at position 415 may be substituted with glutamic acid (E).

In one embodiment of the present invention, the hexuronate C4-epimerase variant may be a hexuronate C4-epimerase variant in which alanine (A) at position 158 from the N-terminal of the hexuronate C4-epimerase having an amino acid sequence set forth in SEQ ID NO: 1 is mutated.

In one embodiment, the hexuronate C4-epimerase variant may be further mutated at serine (S) at position 125, in addition to alanine (A) at position 158.

In one embodiment, the hexuronate C4-epimerase variant may be further mutated at one or more amino acid residues selected from the group consisting of glutamine (Q) at position 149, valine (V) at position 267 and proline (P) at position 351, in addition to alanine (A) at position 158 and serine (S) at position 125. In the hexuronate C4-epimerase variant, glutamine (Q) at position 149 may be substituted with arginine (R), valine (V) at position 267 may be substituted with methionine (M), and proline (P) at position 351 may be substituted with serine (S).

In one embodiment, the hexuronate C4-epimerase variant may be a hexuronate C4-epimerase variant in which proline (P) at position 351 from the N-terminal of the hexuronate C4-epimerase having an amino acid sequence set forth in SEQ ID NO: 1 is mutated.

In one embodiment, the hexuronate C4-epimerase variant may be further mutated at serine (S) at position 125, in addition to proline (P) at position 351.

In one embodiment, the hexuronate C4-epimerase variant may be further mutated at valine (V) at position 267, in addition to proline (P) at position 351 and serine (S) at position 125. Here, the hexuronate C4-epimerase variant may be further mutated at one or more amino acid residues selected from the group consisting of tyrosine (Y) at position 21, valine (V) at position 62, glutamine (Q) at position 149, and leucine (L) at position 316. In the hexuronate C4-epimerase variant, tyrosine (Y) at position 21 may be substituted with phenylalanine (F), valine (V) at position 62 may be substituted with isoleucine (I), glutamine (Q) at position 149 may be substituted with arginine (R), and leucine (L) at position 316 may be substituted with phenylalanine (F).

According to one embodiment of the present invention, the hexuronate C4-epimerase variant may be a hexuronate C4-epimerase variant in which serine (S) at position 125, lysine (K) at position 164, aspartic acid (D) at position 168 and glutamic acid (E) at position 175 from the N-terminal of the hexuronate C4-epimerase having an amino acid sequence set forth in SEQ ID NO: 1 are mutated.

In one embodiment, the hexuronate C4-epimerase variant in which serine (S) at position 125, lysine (K) at position 164, aspartic acid (D) at position 168 and glutamic acid (E) at position 175 are mutated may be further mutated at one or more amino acid residues selected from the group consisting of leucine (L) at position 140, arginine (R) at position 386, serine (S) at position 268 and asparagine (N) at position 297. In the hexuronate C4-epimerase variant, leucine (L) at position 140 may be substituted with proline (P), arginine (R) at position 386 may be substituted with proline (P), or valine (V), serine (S) at position 268 may be substituted with cysteine (C), or threonine (T), and asparagine (N) at position 297 may be substituted with lysine (K).

According to one embodiment of the present invention, the hexuronate C4-epimerase variant may be a hexuronate C4-epimerase variant in which serine (S) at position 125, glutamine (Q) at position 149 and valine (V) at position 267 from the N-terminal of the hexuronate C4-epimerase variant having an amino acid sequence set forth in SEQ ID NO: 1 are mutated.

According to one embodiment of the present invention, the hexuronate C4-epimerase variant has a genetic homology of 50% or more with hexuronate C4-epimerase variants comprised of an amino acid sequence (for example, SEQ ID NO: 3, M125 variant in Table 3) deduced from modified amino acid positions and substituted amino acid residues disclosed in Tables 2 to 5 in an amino acid sequence of wild type hexuronate C4-epimerase (SEQ ID NO: 1), or variants having the disclosed amino acid sequence. According to one embodiment, the hexuronate C4-epimerase variant may have a genetic homology of 60%, 70%, 75%, or 80%. According to another embodiment, the hexuronate C4-epimerase variant may have a genetic homology of 85%, 90%, or 95%. According to a further embodiment, the hexuronate C4-epimerase variant may include a polypeptide moiety having a homology of 97% or 99%.

As used herein, the term "homology" refers to the percent of polypeptide sequence identity between two polypeptide moieties. Homology between one moiety and the other moiety may be determined by a known technique. For example, homology may be determined by directly aligning sequence information between two polypeptide molecules by means of a commercially available computer program. In addition, homology may be determined by hybridizing polynucleotides under the condition of forming stable double strands between homologous regions, digesting the double strands using a single strand specific nuclease and measuring the size of digested fragments.

As used herein, the term "homologue", in all grammatical forms and spelling derivatives thereof, includes superfamily derived proteins (for example, immunoglobulin superfamily) and other species derived homologous proteins (for example, myosin light chain and the like) and refers to a relation of proteins having "a common evolutionary origin". Such proteins (and genes encoding them) have a sequence homology reflected by a high degree of sequence similarity. However, "homologue" used in common meaning and in the present invention refers to "sequence similarity" in associated with the adjective expression "very high" instead of referring to "a common evolutionary origin".

As used herein, the term "sequence similarity" refers to a degree of identity or complementarity between nucleotide sequences and amino acid sequences of proteins having or not having a common evolutionary origin. In one embodiment, when two amino acid sequences having a determined length have sequence similarity of 21% (according to one embodiment, at least about 50%, according to another embodiment, about 75%, 90%, 95%, 96%, 97% or 99%), those two amino acid sequences can be called "substantially homologous" or "substantially similar". Substantially homologous sequences may be identified by using standard software employed in data banks, for example, by comparing sequences by a southern hybridization experiment under severe conditions defined for specific systems. Defined suitable hybridization conditions fall within the range of corresponding techniques (for example, see Sambrook et al., 1989, infra).

The hexuronate C4-epimerase variant has improved unit activity of C4-epimerization that epimerizes D-fructose at C4 into D-tagatose, thereby being capable of producing D-tagatose from D-fructose.

The hexuronate C4-epimerase variant may be derived from hexuronate C4-epimerases of thermophilic microorganisms including thermophilic genus *Rhodothermus*, genus *Thermoanaerobacter*, genus *Thermotoga*, or genus *Dictyoglomus*. Concretely, the hexuronate C4-epimerase variant may be derived from hexuronate C4-epimerases of genus *Thermotoga* microorganisms. More particularly, the hexuronate C4-epimerase variant may be derived from hexuronate C4-epimerases of *Thermotoga neapolitana* or *Thermotoga maritima*.

The hexuronate C4-epimerase produced from thermophilic microorganisms may have identical functions to those of enzymes produced from mesophilic microorganisms (mesophiles) while performing stable reactions under extreme reaction conditions (high temperature and the like). Since the hexuronate C4-epimerase produced from thermophilic microorganisms has many advantages such as prevention of contamination by mesophilic microorganisms, increase in solubility of materials having low solubility in substrates, increase in reaction rate, and the like, the hexuronate C4-epimerase produced from thermophilic microorganisms can overcome industrial disadvantages of mesophilic enzymes.

The hexuronate C4-epimerase variant of the present invention may be obtained by, for example, transforming a strain such as *Escherichia coli* (*E.coli*) with DNA (for example, SEQ ID NO: 4) expressing hexuronate C4-epimerase variants, culturing the transformed strain to obtain a cultured mass, disrupting the cultured mass, and purifying the disrupted mass through a column and the like. The strains for transformation may include *Escherichia coli, Corynebacterum glutamicum, Aspergillus oryzae*, or *Bacillus subtilis* and the like.

Another aspect of the present invention provides a nucleic acid encoding the hexuronate C4-epimerase variant, a transformant including the nucleic acid, or a composition for producing D-tagatose including the hexuronate C4-epimerase variant.

A further aspect of the present invention relates to an expression vector including the nucleic acid encoding the C4-epimerase variant of the present invention. As used herein, the term "vector" refers to an optional media for cloning and/or transferring a nucleotide sequence to an organism, for example a host cell. Vectors may be a replicon which induces binding with other DNA fragments and replication of the bound fragments. The term "replicon" as used herein refers to an optional genetic unit (for example, plasmid, phage, cosmid, chromosome, virus), which can serve as self DNA replication unit in the body, which is capable of being replicated by self regulation. The term "vector" as used herein refers to a viral and non-viral system for introducing a nucleotide sequence to an organism, for example, a host cell in vitro, ex vivo or in vivo. The term "vector" also includes mini-spherical DNA.

As used herein, the term "nucleic acid" includes any form of DNA or RNA. Nucleotides that are basic structural units of nucleic acids include not only natural nucleotides but also variants thereof in which sugars or nucleobases are modified (see: Scheit, Nucleotide Analogs, John Wiley, New York (1980); Uhlman and Peyman, Chemical Reviews, 90:543-584(1990)).

As used herein, the term "transformation" is used to refer to a process for inserting a nucleic acid fragment into a genome of a host organism, resulting in stable heredity, while the term "transformant" as used herein refers to an organism in which a nucleic acid fragment is transferred into a genome, and causes stable heredity. Examples of transformants include, for example, protokayotes or eukaryotes, specifically microorganisms belong to *Enterobacteriaceae* or *Corynebacteriaceae* and the like, more specifically, genus *Escherichia*, genus *Ceratia*, and the like, most specifically *Escherichia coli*.

Methods for transformation of organisms include any methods that can introduce a nucleic acid into an organism, and may be performed by suitable standard techniques known in the art. For instance, methods for transformation may include electroporation, calcium phosphate co-precipitation, retroviral infection, microinjection, DEAE-dextran, and cationic liposome methods, without being limited thereto.

The composition for producing D-tagatose including a hexuronate C4-epimerase variant may further include an optional suitable excipient commonly used in a composition for producing D-tagatose. Such excipient may, for example, be, preservatives, wetting agents, dispersing agents, suspending agents, buffering agents, stabilizers, and isotonic agents, without being limited thereto. The composition may include the hexuronate C4-epimerase variant in amounts of 0.1% by weight to 70% by weight on a solid basis.

Yet another aspect of the present invention provides a method for producing D-tagatose including contacting D-fructose with the hexuronate C4-epimerase variant, the transformant, or the composition for producing D-tagatose including the same to epimerize D-fructose.

[Embodiments]

Hereinafter, the method for producing D-tagatose according to the present invention will be described.

The hexuronate C4-epimerase variant according to the present invention, the transformant including a nucleic acid encoding the same, or a composition for producing D-tagatose including the same can be brought into contact with D-fructose, thereby epimerizing carbon at 4 position of D-fructose.

Generally, monosaccharides can be classified into aldohexoses and ketohexoses. In the present invention, D-fructose as a ketohexose is preferably used to produce D-tagatose.

D-fructose may be obtained by hydrolysis of sucrose or by isomerization of glucose. The present invention provides a method for producing D-tagatose at high yield using common and inexpensive raw materials such as fructose, sucrose, and glucose, thereby enabling production of D-tagatose on a large scale.

The step of epimerizing D-fructose according to the present invention may be performed at a pH of 5 to 8. In another embodiment, epimerization may be performed at a pH 6 to 8. The step of epimerizing D-fructose is performed at 60° C. to 85° C., preferably at 80° C. to 85° C. Within these ranges, enzymatic reaction can be performed at a relatively high temperature, thereby providing effects such as minimization of microorganism contamination, improvement in solubility of fructose used as substrates, and maximization of reaction rate and conversion rate of enzymes.

Further, the step of epimerizing D-fructose may be performed in the presence of D-fructose at a concentration of 10% (w/v) to 50% (w/v). According to one embodiment, the step of epimerizing D-fructose is performed in the presence of D-fructose at a concentration of 20% (w/v) to 50% (w/v), more specifically at a concentration of 20% (w/v) to 40% (w/v). According to the present invention, D-tagatose can be produced from high concentration D-fructose in an economical and efficient manner.

The step of epimerizing D-fructose may be performed in the presence of a metal salt. In one embodiment, the metal salt may include at least one selected from the group consisting of $NiSO_4$, $NiCl_2$, $CoCl_2$, $MnCl_2$, and $ZnSO_4$. For example, $ZnSO_4$ may be used as the metal salt. Since the step of epimerizing D-fructose is performed in the presence of the metal salt, it is possible to enhance conversion activity.

In one embodiment, the method for producing D-tagatose may further include hydrolyzing sucrose to obtain D-fructose before the step of epimerizing D-fructose. Enzymes used in hydrolysis may include at least one selected from the group consisting of β-D-fructosidases such as β-fructofuranosidase, invertase and saccharase; sucrase, α-glucosidase, and α-D-glucohydrolase, without being limited thereto.

In one embodiment, the method for producing D-tagatose may further include isomerizing D-glucose to obtain D-fructose before the step of epimerizing D-fructose. Enzymes used in isomerization may include glucose isomerase or phosphoglucose isomerase, without being limited thereto.

In another embodiment, the method for producing D-tagatose may further include obtaining an epimerized mass after the step of epimerization of D-fructose.

In a further embodiment, the method for producing D-tagatose may further include purifying the epimerized mass obtained after the step of obtaining the epimerized mass.

In yet another embodiment, the method for producing D-tagatose may further include crystallizing the purified epimerized mass after the step of purifying the epimerized mass.

The process of purifying the epimerized mass is not particularly limited, and any typical purification processes used in the art may be used. Examples of the purification process may include chromatography, fractional crystallization, and ion purification, without being limited thereto. These purification processes may be performed alone or in combination thereof. For example, the epimerized mass may be purified by chromatography. Separation of sugars through chromatography may be performed based on weak difference in bonding strength between sugars to be separated and metal ions attached to ion resins.

The method for producing D-tagatose according to one embodiment may further include decoloring, desalting or both decoloring and desalting before or after purification. Through decoloring and/or desalting processes, it is possible to obtain a more purified epimerized mass without impurities.

The purified epimerized mass may be subjected to crystallization after the purified D-tagatose liquid is obtained through concentration and SMB (Simulated Moving Bed) chromatography.

The method for producing D-tagatose according to one embodiment may further include concentration of the separated tagatose liquid before crystallization. Through concentration, the purified tagatose reaction mass may be concentrated to about 2.5 to 3 times an initial concentration thereof and crystallization can be more efficiently performed.

The crystallization process is not particularly limited and may include a typical crystallization process. For example, crystallization may be performed by cooling crystallization. Through the crystallization process, finally purified D-tagatose can be produced at high yield.

The method for producing D-tagatose according to another embodiment may further include reusing unreacted D-fructose after purification in the step of obtaining the epimerized mass, reusing a mother liquor, from which crystals are separated after crystallization in the purification step, or performing both steps. Through these steps, it is possible to obtain D-tagatose at high yield while reducing waste D-fructose, thereby providing an economical advantage.

As used herein, the term "carbon at n-position (hereinafter referred to as Cn)" refers to a carbon position defined in accordance with IUPAC nomenclature, wherein n is an integer of 1 or more. For example, "epimerization at carbon 4 position" is expressed as "C4-epimerization".

An amino acid residue (X) at the n-position from the N-terminal of the hexuronate C4-epimerase having an amino acid sequence set forth in SEQ ID NO: 1 of the present invention can be expressed by nX.

Further, unless there is specific mention regarding substituting amino acids at amino acid residues to be mutated in the present invention, amino acids capable of being replaced at the corresponding positions mentioned in other parts of the specification may be considered.

In the present invention, the amino acids may be expressed by abbreviations as follows.

TABLE 1

| Amino acid | Abbreviation |
|---|---|
| Alanine | A |
| Arginine | R |
| Asparagine | N |
| Aspartic acid | D |
| Cysteine | C |
| Glutamic acid | E |
| Glutamine | Q |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

The present invention can produce hexuronate C4-epimerase variants with improved conversion activity to epimerize carbon 4 position of D-fructose, and thus effectively produce D-tagatose using the produced hexuronate C4-epimerase variants and D-fructose as a raw material. In addition, it is possible to produce D-tagatose in high yield in a cost effective manner, which reduces manufacturing costs.

Hereinafter, the present invention will be described in more detail with reference to some examples. It should be understood that these examples are provided for illustration only and are not to be construed in any way as limiting the present invention.

EXAMPLES

Example 1

Design and Analysis of Improved Target Site

Based on analysis of active site tertiary model structures of orthologs (homologous genes expected to have the same function in other species of microorganisms) which are expected to possess homology with an amino acid sequence of hexuronate C4-epimerase (hereinafter referred to as wild type) derived from *Thermotoga neapolitana*, amino acids expected to be functionally important were primarily selected. Based on analysis results of a docking model between the structure refined after alanine-scanning mutagenesis analysis for the selected amino acids and D-fructose, an improved target site to enhance unit activity of C4-epimerization for D-fructose was designed. Detailed description will be explained below.

Example 1-1

Analysis of Orthologs

Orthologs having a homology with an amino acid sequence (SEQ ID NO: 1) of the wild type were selected from GenBank databases (about 60 orthologs having a sequence coverage of 80% or more and a similarity of 50% or more). Through multiple alignment analysis for the selected orthologs, conserved amino acids expected to be functionally important were identified.

Example 1-2

Analysis of Tertiary Structure Model for Enzyme

Since Protein Data Bank databases showed no protein structure having 30% or more amino acid sequence identity with the wild type and orthologs, it was expected that the model structure for the wild type predicted by a homology modeling could be inaccurate. Accordingly, active site structures between models obtained through various structure modeling servers (RaptorX, Robetta, ModWeb, M4T, HHpred, PHYRE2, I-TASSER, SWISS-MODEL and the like) utilizing various algorithms were compared in order to obtain information for commonly expected structural sites, which was utilized in the next step.

Example 1-3

Alanine-Scanning Mutagenesis and Docking Simulation

Amino acids selected from amino acid sequence analysis between orthologs and the tertiary model structure analysis for active sites were subjected to mutagenesis by substituting each amino acid with alanine to produce recombinant variant enzymes in *Escherichia coli*. Properties of each mutated site were analyzed. Amino acids expected to be functionally important through docking simulation between the model structure refined by alanine-scanning analysis and D-fructose were selected and then an improved target site to enhance unit activity of C4-epimerization for D-fructose was designed. Amino acid residues whose activity was completely eliminated through alanine scanning mutagenesis analysis (suspected to be catalytic metal ion binding residues and catalytic residues involved in deprotonation/protonation) were excluded from the target sites for activity improvement.

Example 2

Preparation of Variant Enzymes and Selection of Variant Enzymes with Improved Activity A single-site saturation mutagenesis library was constructed based on 54 target sites designed in Example 1 (amino acid residues at positions 9, 21, 60, 62, 68, 77, 91, 97, 125, 126, 140, 141, 145, 149, 157, 158, 160, 163, 164, 166, 167, 168, 175, 176, 177, 185, 202, 218, 221, 231, 241, 242, 267, 268, 272, 276, 284, 295, 297, 302, 306, 316, 337, 351, 361, 366, 386, 388, 402, 403, 415, 429, 440 and 441 from the N-terminal of wild type hexuronate C4-epimerase). Thereafter, mutated sites and amino acids having improved unit activity were selected by screening. By incorporating information on the selected improved sites, multiple variant enzymes were prepared. Thereafter, variant enzymes with improved unit activity for D-fructose C4-epimerized conversion were developed.

Example 2-1

Saturation Mutagenesis

A recombinant expression vector prepared for expressing a wild type enzyme gene in *Escherichia coli* BL21(DE3) (a wild type enzyme gene is introduced into a restriction enzyme site of NdeI and XhoI of pET21a, thereby expressing 6xHis-tag recombinant enzyme at C-terminal) was used as a template for saturation mutagenesis for variant library construction. In view of mutation frequency variation and variant yield and the like, inversed PCR based saturation mutagenesis was used (2014. Anal. Biochem. 449:90-98). In order to minimize scales of screening the constructed variant library (minimize the number of codons introduced for saturation mutagenesis), a mixed primer NDTNMA/ATG/TGG (2012. Biotechniques 52:149-158) in which stop codons were excluded and rare codons for E. coli were minimized was designed and used. Specifically, a mixed primer having a total length of 33 bp was constructed using 15 bp residing at the front side of the mutated site, 3 bp to substitute mutation sites (NDT, VMA, ATG and TGG) and 15 bp residing at the rear side of the mutated site. PCR was performed by repeating 30 cycles consisting of denaturing at 94° C. for 2 minutes, denaturing at 94° C. from 30 minutes, annealing at 60° C. for 30 minutes, and extending at 72° C. for 10 minutes, followed by elongation at 72° C. for 60 minutes. After construction of a saturation mutagenesis library for the selected amino acid sites, variants for each library were randomly selected (<11). Base sequences for the variants were analyzed and evaluated as to amino acid mutation frequency. Based on the results, scales of screening each library were set with sequence coverage of 90% or more (2003. Nucleic Acids Res. 15;31:e30).

Example 2-2

Screening for Variant Enzymes with Improved Activity and Preparation of Multiple Variant Enzymes In order to perform high throughput screening of variant enzymes with improved activity from the constructed saturation mutagenesis library on a large scale, a colorimetric method capable of specifically quantifying D-fructose was used. Specifically, 70% Folin-Ciocalteu reagent (SIGMA-ALDRICH) was mixed with a reaction liquid as a substrate in a ratio of 15:1, followed by reacting at 80° C. for 5 minutes, and then optical density (OD) at 900 nm was measured. The obtained OD values were compared and analyzed.

When comparing relative activity with wild type enzyme (SEQ ID NO: 1), 54 variant enzymes with improved activity (conversion of D-tagatose into D-fructose) were initially screened. Corresponding genes were sequenced and then analyzed for amino acid variation (Tables 2 to 5).

The initially selected variant enzymes were reacted with D-fructose using purified enzyme liquid (purified by His-tag affinity chromatography), and then the resultant enzyme reaction products were subjected to HPLC analysis (Shodex SUGAR SP-G column, column analysis temperature: 80° C., mobile phase: H$_2$O, flow rate: 0.6 ml/min, Refractive Index Detector). Based on HPLC analysis results, 222 variant enzymes with increased activity for the production of D-tagatose from D-fructose as compared with a wild type enzyme were finally selected.

Example 3

Comparative Evaluation for Variant Enzymes with Improved Activity

In order to evaluate relative activity of D-fructose C4-epimerization for a variant enzyme at a single site with improved unit activity and a variant enzyme at multiple sites with improved unit activity, each enzyme was expressed in E. coli BL21(DE3), followed by purifying by His-tag affinity chromatography. An enzyme liquid with a concentration of 10 unit/ml was added to a 30% (w/v) D-fructose substrate, followed by reacting at 60° C. and pH 7.0 [50 mM potassium phosphate buffer solution] for two hours, thereby measuring relative activity of D-fructose C4-epimerization for a variant enzyme as compared with *Thermotoga neapolitana* derived wild type recombinant enzyme (wild type, SEQ ID NO: 1).

TABLE 2

| name | 77 | 125 | 149 | 158 | 185 | 267 | 268 | 272 | 351 | 403 | Mutation Number | Relative Activity |
|---|---|---|---|---|---|---|---|---|---|---|---|---|
| WT | | | | | | | | | | | — | 100 |
| M1 | | C | | | | | | | | | 1 | 193 |
| M2 | | Y | | | | | | | | | 1 | 116 |
| M3 | | Q | | | | | | | | | 1 | 165 |
| M4 | | E | | | | | | | | | 1 | 202 |
| M5 | | T | | | | | | | | | 1 | 211 |
| M6 | | N | | | | | | | | | 1 | 131 |
| M7 | | D | | | | | | | | | 1 | 303 |
| M8 | | | | | K | | | | | | 1 | 114 |
| M9 | | | | | R | | | | | | 1 | 114 |
| M10 | | | | | H | | | | | | 1 | 118 |
| M11 | | | | | Q | | | | | | 1 | 107 |
| M12 | | | | | A | | | | | | 1 | 102 |
| M13 | | | | | | | | F | | | 1 | 104 |
| M14 | | | | | | | | E | | | 1 | 120 |
| M15 | | | | | | | | D | | | 1 | 121 |
| M16 | | | | | | | | Q | | | 1 | 116 |
| M17 | | | | | | | | S | | | 1 | 133 |
| M18 | | | | | | | | V | | | 1 | 117 |
| M19 | | | | | | | | R | | | 1 | 105 |
| M20 | | | | | | | | K | | | 1 | 117 |
| M21 | | | | | | | | | | S | 1 | 114 |
| M22 | | | | | | | | | | T | 1 | 130 |
| M23 | | | | | | | | | | Q | 1 | 119 |
| M24 | | | | | | | | | | F | 1 | 110 |
| M25 | | | | | | | | | | V | 1 | 117 |
| M26 | | | | | | | | | | I | 1 | 128 |
| M27 | | | | | | | | | | A | 1 | 119 |
| M28 | P | D | | | | | | | | | 2 | 479 |

TABLE 2-continued

| name | 77 | 125 | 149 | 158 | 185 | 267 | 268 | 272 | 351 | 403 | Mutation Number | Relative Activity |
|---|---|---|---|---|---|---|---|---|---|---|---|---|
| M29 | P | D | | | | | | | | | 2 | 487 |
| M30 | R | D | | | | | | | | | 2 | 426 |
| M31 | | D | | T | | | | | | | 2 | 494 |
| M32 | | D | | | K | | | | | | 2 | 543 |
| M33 | | D | | | R | | | | | | 2 | 430 |
| M34 | | D | | | H | | | | | | 2 | 493 |
| M35 | | D | | | Q | | | | | | 2 | 584 |
| M36 | | D | | | A | | | | | | 2 | 447 |
| M37 | | D | | | G | | | | | | 2 | 481 |
| M38 | | D | | | | | | | S | | 2 | 421 |
| M39 | | D | | | | | | | | S | 2 | 377 |
| M40 | | D | | | | | | | | T | 2 | 431 |
| M41 | | D | | | | | | | | Q | 2 | 371 |
| M42 | R | D | | T | | | | | | | 3 | 572 |
| M43 | P | D | | T | | | | | | | 3 | 452 |
| M44 | P | D | | | | | | | S | | 3 | 473 |
| M45 | | D | R | T | | | | | | | 3 | 557 |
| M46 | | D | R | | M | | | | | | 3 | 594 |
| M47 | | D | | T | M | | | | | | 3 | 608 |
| M48 | | D | | T | | | | | S | | 3 | 605 |
| M49 | | D | | T | | | | | S | | 3 | 480 |
| M50 | | D | | | Q | C | | | | | 3 | 422 |
| M51 | | D | | | Q | C | | | | | 3 | 422 |
| M52 | | D | | | K | | D | | | | 3 | 638 |
| M53 | | D | | | K | | V | | | | 3 | 402 |
| M54 | | D | | | K | | I | | | | 3 | 515 |
| M55 | | D | | | K | | L | | | | 3 | 506 |
| M56 | | D | | | K | | M | | | | 3 | 540 |
| M57 | | D | | | K | | Q | | | | 3 | 628 |
| M58 | | D | | | K | | | | | T | 3 | 790 |
| M59 | | D | | | Q | | | | | T | 3 | 746 |
| M60 | | D | | | M | | | | S | | 3 | 613 |

TABLE 3

| name | 9 | 21 | 60 | 62 | 68 | 77 | 91 | 97 | 125 | 140 | 141 | 149 | 158 | 164 | 166 | 168 | 175 | 176 |
|---|---|---|---|---|---|---|---|---|---|---|---|---|---|---|---|---|---|---|
| WT | | | | | | | | | | | | | | | | | | |
| M42 | | | | | | R | | | D | | | | T | | | | | |
| M43 | | | | | | P | | | D | | | | T | | | | | |
| M44 | | | | | | P | | | D | | | | | | | | | |
| M45 | | | | | | | | | D | | | R | T | | | | | |
| M46 | | | | | | | | | D | | | R | | | | | | |
| M47 | | | | | | | | | D | | | | T | | | | | |
| M48 | | | | | | | | | D | | | | T | | | | | |
| M49 | | | | | | | | | D | | | | T | | | | | |
| M50 | | | | | | | | | D | | | | | | | | | |
| M51 | | | | | | | | | D | | | | | | | | | |
| M52 | | | | | | | | | D | | | | | | | | | |
| M53 | | | | | | | | | D | | | | | | | | | |
| M54 | | | | | | | | | D | | | | | | | | | |
| M55 | | | | | | | | | D | | | | | | | | | |
| M56 | | | | | | | | | D | | | | | | | | | |
| M57 | | | | | | | | | D | | | | | | | | | |
| M58 | | | | | | | | | D | | | | | | | | | |
| M59 | | | | | | | | | D | | | | | | | | | |
| M60 | | | | | | | | | D | | | | | | | | | |
| M61 | | | | | | | R | | D | | | | T | | | | | |
| M62 | | | | | | | | | D | | | | | | | | | |
| M63 | | | | | | | | | D | | | | | | | | | |
| M64 | | | | | | | R | | D | | | | T | | | | | |
| M65 | | | | | | | | | D | | | | | | | | | |
| M66 | | | | | | | | | D | | | | | | | | | |
| M67 | | | | | | | | | D | | | | | | | | | |
| M68 | | | | | | | | | D | | | | | | | | | |
| M69 | | | | | | | | | D | | | | | | | | | |
| M70 | Y | | | D | | P | | | D | | | | T | | | | | |
| M71 | | | G | | | | | | D | | | | | | | | | |
| M72 | | | | | L | | | | D | | | | | | | | | |
| M73 | | | | | | | | | D | P | | | | M | E | G | | |
| M74 | | | | | | | | | D | | R | | | | | | | |
| M75 | | | | | | | | | D | | | | | M | E | G | | |
| M76 | | | | | | | | | D | | | | | | R | | | |
| M77 | | | | | | | | | D | | | | | | | | | |

TABLE 3-continued

| name | c1 | c2 | c3 | c4 | c5 | c6 | c7 | c8 | c9 | c10 | c11 |
|---|---|---|---|---|---|---|---|---|---|---|---|
| M78 | | | | | D | | | | | | |
| M79 | | | | | D | | | | | | |
| M80 | F | I | | | D | | R | | | | |
| M81 | F | I | | | D | | R | | | | |
| M82 | F | I | | | D | | R | | | | |
| M83 | F | I | | | D | | R | | | | |
| M84 | | | | W | D | | | | | | |
| M85 | | I | | | D | | | | | | |
| M86 | | | N | | D | | | | | | |
| M87 | | | | | D | F | | | | | |
| M88 | | | | | D | | | M | E | G | |
| M89 | | | | | D | | | | | | H |
| M90 | | | | | D | | | | | | F |
| M91 | | | | | D | | | | | | Y |
| M92 | | | | | D | | | | | | |
| M93 | | | | | D | | | | | | |
| M94 | | | | | D | | | | | | |
| M95 | | | | | D | | | | | | |
| M96 | | | | | D | | | | | | |
| M97 | | | | | D | | | | | | |
| M98 | | | | | D | | | | | | |
| M99 | | | | | D | | | | | | |
| M100 | | | | | D | | | | | | |
| M101 | | | | | D | | | | | | |
| M102 | | | | | D | | | | | | |
| M103 | | | | | D | | | | | | |
| M104 | | | | | D | | | | | | |
| M105 | | | | | D | | | | | | |
| M106 | | | | | D | | | | | | |
| M107 | | | | | D | | | | | | |
| M108 | | | | | D | | | | | | |
| M109 | | | | | D | | | | | | |
| M110 | | | | | D | | | | | | |
| M111 | | | | | D | | | | | | |
| M112 | | | | | D | | | | | | |
| M113 | | | | | D | | | | | | |
| M114 | | | | | | | | | | | |

| name | 185 | 231 | 267 | 268 | 272 | 297 | 306 | 316 | 351 | 386 | 403 | 415 | Mutation Number | Relative Activity |
|---|---|---|---|---|---|---|---|---|---|---|---|---|---|---|
| WT | | | | | | | | | | | | | — | 100 |
| M42 | | | | | | | | | | | | | 3 | 572 |
| M43 | | | | | | | | | | | | | 3 | 452 |
| M44 | | | | | | | | | | S | | | 3 | 473 |
| M45 | | | | | | | | | | | | | 3 | 557 |
| M46 | | M | | | | | | | | | | | 3 | 594 |
| M47 | | M | | | | | | | | | | | 3 | 608 |
| M48 | | | | | | | | | | S | | | 3 | 605 |
| M49 | | | | | | | | | | S | | | 3 | 480 |
| M50 | Q | | | C | | | | | | | | | 3 | 422 |
| M51 | Q | | | C | | | | | | | | | 3 | 422 |
| M52 | K | | | | D | | | | | | | | 3 | 638 |
| M53 | K | | | | V | | | | | | | | 3 | 402 |
| M54 | K | | | | I | | | | | | | | 3 | 515 |
| M55 | K | | | | L | | | | | | | | 3 | 506 |
| M56 | K | | | | M | | | | | | | | 3 | 540 |
| M57 | K | | | | Q | | | | | | | | 3 | 628 |
| M58 | | | | | | | | | | | T | | 3 | 790 |
| M59 | Q | | | | | | | | | | T | | 3 | 746 |
| M60 | | M | | | | | | | | S | | | 3 | 613 |
| M61 | | | | | | | | | | | T | | 4 | 441 |
| M62 | Q | | | | H | | M | | | | | | 4 | 495 |
| M63 | Q | | | | D | | M | | | | | | 4 | 548 |
| M64 | | | | | | | | | | V | T | | 5 | 437 |
| M65 | Q | | | C | D | | M | | | | | | 5 | 526 |
| M66 | Q | | M | T | D | | | | | | | | 5 | 451 |
| M67 | | R | M | T | D | | | | | | | | 5 | 510 |
| M68 | | | M | T | D | | | | | V | | | 5 | 555 |
| M69 | | | M | | | | | | S | V | T | | 5 | 445 |
| M70 | | | | | | | | | | | | E | 6 | 427 |
| M71 | Q | | M | | | | M | | | | T | | 6 | 489 |
| M72 | | | M | T | D | | | | | V | | | 6 | 695 |
| M73 | | | | | | | | | | V | | | 6 | 564 |
| M74 | | | M | T | D | | | | | V | | | 6 | 496 |
| M75 | | | | T | | K | | | | | | | 6 | 498 |
| M76 | | | M | T | D | | | | | V | | | 6 | 592 |
| M77 | Q | | M | T | D | | | | | | T | | 6 | 691 |
| M78 | | | M | T | D | | | | S | V | | | 6 | 553 |
| M79 | Q | | M | C | D | | M | | | | | | 6 | 588 |

TABLE 3-continued

| name | c1 | c2 | c3 | c4 | c5 | c6 | c7 | c8 | count | value |
|---|---|---|---|---|---|---|---|---|---|---|
| M80 |  | M |  |  |  | F | S |  | 7 | 540 |
| M81 |  | M |  |  |  | F | S |  | 7 | 454 |
| M82 |  | M |  |  |  | F | S |  | 7 | 498 |
| M83 |  | M |  |  |  | F | s |  | 7 | 500 |
| M84 | Q | M | T | D |  |  |  | T | 7 | 478 |
| M85 | Q | M | T | D |  |  |  | T | 7 | 560 |
| M86 | Q | M | T | D |  |  |  | T | 7 | 486 |
| M87 | Q | M | T | D |  |  |  | T | 7 | 496 |
| M88 |  | M | C | D |  |  |  |  | 7 | 437 |
| M89 | Q | M | T | D |  |  |  | I | 7 | 610 |
| M90 | Q | M | T | D |  |  |  | I | 7 | 539 |
| M91 | Q | M | T | D |  |  |  | I | 7 | 662 |
| M92 | Q | M | T | D | M |  |  | Q | 7 | 822 |
| M93 | Q | M | T | D | M |  |  | I | 7 | 1011 |
| M94 | Q | M | T | D | M |  |  | L | 7 | 728 |
| M95 | Q | M | T | D | M |  |  | A | 7 | 749 |
| M96 | Q | M | T | D | M |  |  | P | 7 | 728 |
| M97 | Q | M | T | D | M |  |  | V | 7 | 1023 |
| M98 | Q | M | T | D | M |  |  | W | 7 | 682 |
| M99 | Q | M | T | D | M |  |  | R | 7 | 607 |
| M100 | Q | M | T | D | M |  |  | H | 7 | 948 |
| M101 | Q | M | T | D | M |  |  | F | 7 | 956 |
| M102 | Q | M | T | D | M |  |  | K | 7 | 536 |
| M103 | Q | M | T | D | M |  |  | N | 7 | 932 |
| M104 | Q | M | T | D | M |  |  | E | 7 | 400 |
| M105 | Q | M | T | D | M |  |  | D | 7 | 476 |
| M106 | Q | M | T | D | M |  |  | C | 7 | 457 |
| M107 | Q | M | T | D | M |  |  | T | 7 | 690 |
| M108 | Q | M | T | D | M |  | V |  | 7 | 326 |
| M109 | Q | M | T | D |  |  | V | T | 7 | 693 |
| M110 | Q | M | T |  | M |  | V | T | 7 | 822 |
| M111 | Q | M |  | D | M |  | V | T | 7 | 558 |
| M112 | Q |  | T | D | M |  | V | T | 7 | 655 |
| M113 |  | M | T | D | M |  | V | T | 7 | 597 |
| M114 | Q | M | T | D | M |  | V | T | 7 | 589 |

TABLE 4

| name | 60 | 97 | 125 | 126 | 145 | 163 | 164 | 166 | 168 | 175 | 185 | 202 | 221 | 231 | 241 | 242 | 267 | 268 | 272 |
|---|---|---|---|---|---|---|---|---|---|---|---|---|---|---|---|---|---|---|---|
| WT |  |  |  |  |  |  |  |  |  |  |  |  |  |  |  |  |  |  |  |
| M115 |  |  | D | G |  |  |  |  |  |  | Q |  |  |  |  |  | M | T | D |
| M116 |  |  | D |  |  |  | M |  | E | G |  |  |  |  |  |  |  | T |  |
| M117 |  |  | D |  |  | R |  |  |  |  | Q |  |  |  |  |  | M | T | D |
| M118 |  |  | D |  |  |  |  |  |  |  | Q |  |  | R |  |  | M | T | D |
| M119 |  |  | D |  |  |  |  |  |  |  | Q |  |  |  |  |  | M | T | G |
| M120 |  |  | D |  |  |  |  |  |  |  | Q |  |  |  |  |  | M | T | D |
| M121 |  |  | D |  |  |  |  |  |  |  | Q |  |  |  |  |  | M | T | D |
| M122 |  |  | D |  |  |  |  |  |  |  | Q |  |  |  |  |  | M | T | D |
| M123 |  |  | D |  |  |  |  |  |  |  | Q |  |  |  |  |  | M | T | D |
| M124 |  |  | D |  |  |  |  |  |  |  | Q |  |  |  |  |  | M | T | D |
| M125 |  |  | D |  |  |  |  |  |  |  | Q |  |  |  |  |  | M | T | D |
| M126 |  |  | D |  |  |  |  |  |  |  | Q |  |  |  |  |  | M | T | V |
| M127 |  |  | D |  |  |  |  |  |  |  | Q |  |  |  |  |  | M | T | A |
| M128 |  |  | D |  |  |  |  |  |  |  | Q |  |  |  |  |  | M | C | D |
| M129 |  |  | D |  |  |  |  |  |  |  | Q |  |  |  |  |  | M | T | E |
| M130 |  |  | D |  |  |  |  |  |  |  | Q |  |  |  |  |  | M | T | D |
| M131 |  |  | D |  |  |  |  |  |  |  | Q |  |  |  |  |  | M | T | D |
| M132 |  |  | D |  |  |  |  |  |  |  | Q |  |  |  |  |  | M | T |  |
| M133 |  |  | D |  |  |  |  |  |  |  |  |  |  |  |  |  | M | C | D |
| M134 | D |  | D |  |  |  |  |  |  |  |  | T | F |  |  | F | M | T |  |
| M135 |  | A | D |  |  |  |  |  |  |  | Q |  |  |  |  |  | M | T | D |
| M136 |  | L | D |  |  |  |  |  |  |  | Q |  |  |  |  |  | M | T | D |
| M137 |  |  | D | F |  |  |  |  |  |  | Q |  |  |  |  |  | M | T | D |
| M138 |  |  | D | L |  |  |  |  |  |  | Q |  |  |  |  |  | M | T | D |
| M139 |  |  | D | P |  |  |  |  |  |  | Q |  |  |  |  |  | M | T | D |
| M140 |  |  | D | I |  |  |  |  |  |  | Q |  |  |  |  |  | M | T | D |
| M141 |  |  | D | T |  |  |  |  |  |  | Q |  |  |  |  |  | M | T | D |
| M142 |  |  | D | A |  |  |  |  |  |  | Q |  |  |  |  |  | M | T | D |
| M143 |  |  | D | G |  |  |  |  |  |  | Q |  |  |  |  |  | M | T | D |
| M144 |  |  | D | R |  |  |  |  |  |  | Q |  |  |  |  |  | M | T | D |
| M145 |  |  | D |  | A |  |  |  |  |  | Q |  |  |  |  |  | M | T | D |
| M146 |  |  | D |  |  | A |  |  |  |  | Q |  |  |  |  |  | M | T | D |
| M147 |  |  | D |  |  | Q |  |  |  |  | Q |  |  |  |  |  | M | T | D |
| M148 |  |  | D |  |  |  | M |  |  |  | Q |  |  |  |  |  | M | T | D |
| M149 |  |  | D |  |  |  |  | R |  |  | Q |  |  |  |  |  | M | T | D |
| M150 |  |  | D |  |  |  |  |  |  |  | Q |  |  | R |  |  | M | T | D |

TABLE 4-continued

| name | | | | | | | |
|---|---|---|---|---|---|---|---|
| M151 | D | | | Q | | N | M T D |
| M152 | D | | | Q | | T | M T D |
| M153 | D | | | Q | | S | M T D |
| M154 | D | | | Q | | | M T D |
| M155 | D | | | Q | | | M T D |
| M156 | D | | | Q | | | M T D |
| M157 | D | | | Q | | | M T D |
| M158 | D | | | Q | | | M T D |
| M159 | D | | | Q | | | M T D |
| M160 | D | | | Q | | | M T D |
| M161 | D | | | Q | | | M T D |
| M162 | D | | | Q | | | M T D |
| M163 | D | | | Q | | | M T D |
| M164 | D | | | Q | | | M T D |
| M165 | D | | | Q | | | M T D |
| M166 | D | | | Q | | | M T D |
| M167 | D | | | Q | | | M T D |
| M168 | D | | | Q | | | M T D |

| name | 276 | 284 | 297 | 306 | 337 | 366 | 386 | 388 | 402 | 403 | 415 | 429 | 440 | Mutation Number | Relative Activity |
|---|---|---|---|---|---|---|---|---|---|---|---|---|---|---|---|
| WT | | | | | | | | | | | | | | — | 100 |
| M115 | | | | | | V | | | | T | | | | 8 | 521 |
| M116 | | K | | | | | | V | | T | | | | 8 | 445 |
| M117 | | | M | | | | | | | T | | | | 8 | 697 |
| M118 | | | M | | | | | | | T | | | | 8 | 640 |
| M119 | | | M | | | V | | | | M | | | | 8 | 487 |
| M120 | | | M | | | V | | | | M | | | | 8 | 786 |
| M121 | | | M | | | V | | | | G | | | | 8 | 808 |
| M122 | | | H | | | V | | | | T | | | | 8 | 440 |
| M123 | | | V | | | V | | | | T | | | | 8 | 649 |
| M124 | | | F | | | V | | | | T | | | | 8 | 740 |
| M125 | | | M | | | V | | | | I | | | | 8 | 1006 |
| M126 | | | M | | | V | | | | I | | | | 8 | 699 |
| M127 | | | M | | | V | | | | I | | | | 8 | 540 |
| M128 | | | M | | | V | | | | T | | | | 8 | 495 |
| M129 | | | M | | | V | | | | I | | | | 8 | 931 |
| M130 | | | M | | | V | | | | G | | | | 8 | 557 |
| M131 | | | M | | | V | | | | D | | | | 8 | 625 |
| M132 | | | M | | | V | | | | N | | | | 8 | 408 |
| M133 | | A | M | | | | | | | T | E | | | 8 | 418 |
| M134 | | | | | | | P | | | T | | | | 9 | 643 |
| M135 | | | M | | | V | | | | T | | | | 9 | 672 |
| M136 | | | M | | | V | | | | T | | | | 9 | 695 |
| M137 | | | M | | | V | | | | T | | | | 9 | 661 |
| M138 | | | M | | | V | | | | T | | | | 9 | 656 |
| M139 | | | M | | | V | | | | T | | | | 9 | 636 |
| M140 | | | M | | | V | | | | T | | | | 9 | 667 |
| M141 | | | M | | | V | | | | T | | | | 9 | 670 |
| M142 | | | M | | | V | | | | T | | | | 9 | 518 |
| M143 | | | M | | | V | | | | I | | | | 9 | 682 |
| M144 | | | M | | | V | | | | I | | | | 9 | 553 |
| M145 | | | M | | | V | | | | T | | | | 9 | 553 |
| M146 | | | M | | | V | | | | T | | | | 9 | 664 |
| M147 | | | M | | | V | | | | T | | | | 9 | 597 |
| M148 | | | M | | | V | | | | T | | | | 9 | 634 |
| M149 | | | M | | | V | | | | T | | | | 9 | 752 |
| M150 | | | M | | | V | | | | T | | | | 9 | 733 |
| M151 | | | M | | | V | | | | I | | | | 9 | 699 |
| M152 | | | M | | | V | | | | I | | | | 9 | 697 |
| M153 | | | M | | | V | | | | I | | | | 9 | 736 |
| M154 | E | | M | | | V | | | | I | | | | 9 | 601 |
| M155 | A | | M | | | V | | | | I | | | | 9 | 586 |
| M156 | | | M | | T | V | | | | I | | | | 9 | 1093 |
| M157 | | | M | | Y | V | | | | I | | | | 9 | 1093 |
| M158 | | | M | | N | V | | | | I | | | | 9 | 1489 |
| M159 | | | M | | P | V | | | | I | | | | 9 | 1408 |
| M160 | | | M | | S | V | | | | I | | | | 9 | 1180 |
| M161 | | | M | | S | V | | | | I | | | | 9 | 771 |
| M162 | | | M | | G | V | | | | I | | | | 9 | 367 |
| M163 | | | M | | C | V | | | | I | | | | 9 | 476 |
| M164 | | | M | | | V | | | F | I | | | | 9 | 677 |
| M165 | | | M | | | V | | | C | I | | | | 9 | 658 |
| M166 | | | M | | | V | | | Y | I | | | | 9 | 644 |
| M167 | | | M | | | V | | | | T | | P | | 9 | 585 |
| M168 | | | M | | | V | | | | T | | | A | 9 | 764 |

TABLE 5

| name | 97 | 125 | 157 | 160 | 163 | 164 | 166 | 167 | 177 | 202 | 218 | 231 | 267 | 268 | 272 | 295 | 302 | 306 | 337 | 361 | 366 | 386 | 403 | 441 | Mutation Number | Relative Activity |
|---|---|---|---|---|---|---|---|---|---|---|---|---|---|---|---|---|---|---|---|---|---|---|---|---|---|---|
| WT | L | | | | | | | | | | | | | | | | | | | | | | | | — | 100 |
| M169 | L | D | | | | | | | | | | | M | T | D | | | M | | | | V | T | | 10 | 550 |
| M170 | L | D | | | | | | | | | | | M | T | D | | | M | | | | V | T | | 10 | 706 |
| M171 | L | D | R | | | | | | | | | | M | T | D | | | M | | | | V | T | | 10 | 613 |
| M172 | | D | | L | | | | | | | | | M | T | D | | | M | W | | | V | I | | 10 | 1268 |
| M173 | | D | | F | | | | | | | | | M | T | D | | | M | W | | | V | I | | 10 | 1429 |
| M174 | | D | | R | | | | | | | | | M | T | D | | | M | W | | | V | I | | 10 | 982 |
| M175 | | D | | Y | | | | | | | | | M | T | D | | | M | | | | V | T | | 10 | 565 |
| M176 | | D | | | | M | | | | | | | M | T | D | | | M | W | | | V | I | | 10 | 668 |
| M177 | | D | | | M | | | | | | | | M | T | D | | | M | W | | | V | I | | 10 | 617 |
| M178 | | D | | | | | R | | | | | R | M | T | D | | | M | W | | | V | I | | 10 | 1803 |
| M179 | | D | | | | | | A | | | | | M | T | D | | | M | W | | | V | I | | 10 | 1854 |
| M180 | | D | | | | | | W | | | | | M | T | D | | | M | W | | | V | I | | 10 | 1678 |
| M181 | | D | | | | | | I | | | | | M | T | D | | | M | W | | | V | I | | 10 | 1432 |
| M182 | | D | | | | | | K | | | | | M | T | D | | | M | W | | | V | I | | 10 | 1770 |
| M183 | | D | | | | | | M | | | | | M | T | D | | | M | W | | | V | I | | 10 | 1351 |
| M184 | | D | | | | | | V | | | | | M | T | D | | | M | W | | | V | I | | 10 | 1951 |
| M185 | | D | | | | | | S | | | | | M | T | D | | | M | W | | | V | I | | 10 | 911 |
| M186 | | D | | | | | | | Y | | | | M | T | D | | | M | W | | | V | I | | 10 | 733 |
| M187 | | D | | | | | | | H | | | | M | T | D | | | M | W | | | V | I | | 10 | 1489 |
| M188 | | D | | | | | | | L | | | | M | T | D | | | M | W | | | V | I | | 10 | 818 |
| M189 | | D | | | | | | | | | I | | M | T | D | | | M | W | | | V | I | | 10 | 1294 |
| M190 | | D | | | | | | | | | S | | M | T | D | | | M | W | | | V | I | | 10 | 1348 |
| M191 | | D | | | | | | | | | L | | M | T | D | | | M | W | | | V | I | | 10 | 1350 |
| M192 | | D | | | | | | | | | F | | M | T | D | | | M | W | | | V | I | | 10 | 1204 |
| M193 | | D | | | | | | | | | C | | M | T | D | | | M | W | | | V | I | | 10 | 1000 |
| M194 | | D | | | | | | | | | | | M | T | D | C | | M | W | | | V | I | | 10 | 485 |
| M195 | | D | | | | | | | | | | | M | T | D | R | | M | W | | | V | I | | 10 | 1261 |
| M196 | | D | | | | | | | | | | | M | T | D | Y | | M | W | | | V | I | | 10 | 1222 |
| M197 | | D | | | | | | | | | | | M | T | D | | C | M | W | | | V | I | | 10 | 966 |
| M198 | | D | | | | | | | | | | | M | T | D | | | M | W | K | | V | I | | 10 | 630 |
| M199 | | D | | | | | | | | | | | M | T | D | | | M | W | E | | V | I | | 10 | 586 |
| M200 | | D | | | | | | | | | | | M | T | D | | | M | W | V | | V | I | | 10 | 783 |
| M201 | | D | | | | | | | | | | | M | T | D | | | M | W | W | | V | I | | 10 | 781 |
| M202 | | D | | | | | | | | | | | M | T | D | | | M | W | Y | | V | I | | 10 | 549 |
| M203 | | D | | | | | | | | | | | M | T | D | | | M | W | M | | V | I | | 10 | 760 |
| M204 | | D | | | | | | | | | | | M | T | D | | | M | W | R | | V | I | | 10 | 731 |
| M205 | | D | | | | | | | | | | | M | T | D | | | M | W | Q | | V | I | | 10 | 638 |
| M206 | | D | | | | | | | | | | | M | T | D | | | M | W | L | | V | I | | 10 | 879 |
| M207 | | D | | | | | | | | | | | M | T | D | | | M | W | R | | V | I | | 10 | 1428 |
| M208 | | D | | | | | | | | | | | M | T | D | | | M | W | Y | | V | I | | 10 | 856 |
| M209 | | D | | | | | | | | | | | M | T | D | | | M | W | C | | V | I | | 10 | 589 |
| M210 | | D | | | | | | | | | | | M | T | D | | | M | W | L | | V | I | | 10 | 1306 |
| M211 | | D | | | | | | | | | | | M | T | D | | | M | F | | S | V | I | | 10 | 1246 |
| M212 | | D | | | | | | | | | | | M | T | D | | | M | E | | S | V | I | | 10 | 1271 |
| M213 | | D | | | | | | | | | | | M | T | D | | | M | S | | S | V | I | | 10 | 1306 |
| M214 | | D | | | | | | | | | | | M | T | D | | | M | W | | | V | I | E | 10 | 1160 |
| M215 | | D | | | | | | | | | | | M | T | D | | | M | W | | | V | I | W | 10 | 1150 |

TABLE 5-continued

| name | 97 | 125 | 157 | 160 | 163 | 164 | 166 | 167 | 177 | 202 | 218 | 231 | 267 | 268 | 272 | 295 | 302 | 306 | 337 | 361 | 366 | 386 | 403 | 441 | Mutation Number | Relative Activity |
|---|---|---|---|---|---|---|---|---|---|---|---|---|---|---|---|---|---|---|---|---|---|---|---|---|---|---|
| M216 | | D | | | | | | | | | | | M | T | D | | | M | W | | | V | I | H | 10 | 1250 |
| M217 | | D | | | | | | | | | | | M | T | D | | | M | W | | | V | I | K | 10 | 1270 |
| M218 | | D | | | | | | | | | | | M | T | D | | | M | W | | | V | I | A | 10 | 1250 |
| M219 | | D | | | | | | | | | | | M | T | D | | | M | W | | | V | I | R | 10 | 1220 |
| M220 | | D | | | | | | | | | | | M | T | D | | | M | W | | | V | I | S | 10 | 1449 |
| M221 | | D | | | | | | | | | | | M | T | D | | | M | W | | | V | I | F | 10 | 1294 |

As can be seen from the above results, it was confirmed that C4-epimerase variants according to the present invention possess improved D-fructose C4-epimeraization activity as compared to a wild type enzyme, specifically, M184 enzyme variant exhibited about 20 fold increase in D-tagatose production activity as compared to a wild type enzyme.

Although some embodiments have been described herein, it should be understood by those skilled in the art that these embodiments are given by way of illustration only, and that various modifications, variations, and alterations can be made without departing from the spirit and scope of the invention. Therefore, the scope of the invention should be limited only by the accompanying claims and equivalents thereof.

The invention claimed is:

1. A hexuronate C4-epimerase variant having the amino acid sequence set forth in SEQ ID NO: 1, in which a serine (S) amino acid residue at position 125 is substituted with cysteine (C), tyrosine (Y), glutamine (Q), glutamic acid (E), threonine (T), asparagine (N), or aspartic acid (D) from an N-terminal of hexuronate C4-epimerase, wherein the variant has an hexuronate C4-epimerase activity.

2. The hexuronate C4-epimerase variant according to claim 1, wherein the serine (S) amino acid residue at position 125 is substituted with aspartic acid (D).

3. The hexuronate C4-epimerase variant according to claim 2, wherein an alanine (A) amino acid residue at position 158 is further substituted with threonine (T).

4. The hexuronate C4-epimerase variant according to claim 3, wherein (i) a glutamine (Q) amino acid residue at position 149 is further substituted with arginine (R), (ii) a valine (V) amino acid residue at position 267 is further substituted with methionine (M), or (iii) a proline (P) amino acid residue at position 351 is further substituted with serine (S).

5. The hexuronate C4-epimerase variant according to claim 2, wherein (i) a glutamine (Q) amino acid residue at position 149 is substituted with arginine (R), and a valine (V) amino acid residue at position 267 is substituted with methionine (M); or (ii) a valine (V) amino acid residue at position 267 is substituted with methionine (M), and a proline (P) amino acid residue at position 351 is further substituted with serine (S).

6. The hexuronate C4-epimerase variant according to claim 2, wherein a lysine (K) amino acid residue at position 164 is substituted with methionine (M), an aspartic acid (D) amino acid residue at position 168 is substituted with glutamic acid (E), and a glutamic acid (E) amino acid residue at position 175 is further substituted with glycine (G); and
  (i) a leucine (L) amino acid residue at position 140 is substituted with proline (P), and an arginine (R) amino acid residue at position 386 is substituted with valine (V); or
  (ii) a serine (S) amino acid residue at position 268 is substituted with threonine (T), and a phenylalanine (F) amino acid residue at position 297 is substituted with lysine (K).

7. The hexuronate C4-epimerase variant according to claim 2, wherein a valine (V) amino acid residue at position 267 is substituted with methionine (M), a serine (S) amino acid residue at position 268 is substituted with threonine (T), and a threonine (T) amino acid residue at position 272 is further substituted with aspartic acid (D); and
  (i) a glutamine (Q) amino acid residue at position 149 is substituted with arginine (R), and an arginine (R) amino acid residue at position 386 is substituted with valine (V);
  (ii) a proline (P) amino acid residue at position 166 is substituted with arginine (R), and an arginine (R) amino acid residue at position 386 is substituted with valine (V);
  (iii) a serine (S) amino acid residue at position 185 is substituted with glutamine (Q), and a tyrosine (Y) amino acid residue at position 403 is substituted with threonine (T); or
  (iv) a proline (P) amino acid residue at position 351 is substituted with serine (S), and an arginine (R) amino acid residue at position 386 is substituted with valine (V).

8. The hexuronate C4-epimerase variant according to claim 2, wherein a valine (V) amino acid at position 267 is substituted with methionine (M), a serine (S) amino acid residue at position 268 is substituted with cysteine (C), a threonine (T) amino acid residue at position 272 is substituted with aspartic acid (D), a serine (S) amino acid residue at position 185 is substituted with glutamine (Q), and a tryptophan (W) amino acid at position 306 is further substituted with methionine (M).

9. The hexuronate C4-epimerase variant according to claim 2, wherein a tyrosine (Y) amino acid residue at position 21 is substituted with phenylalanine (F), a valine (V) amino acid at position 62 is substituted with isoleucine (I), a glutamine (Q) amino acid residue at position 149 is substituted with arginine (R), a valine (V) amino acid residue at position 267 is substituted with methionine (M), a leucine (L) amino acid residue at position 316 is substituted with phenylalanine (F), and a proline (P) amino acid residue at position 351 is further substituted with serine (S).

10. A nucleic acid encoding the hexuronate C4-epimerase variant according to claim 1.

11. A transformant comprising the nucleic acid according to claim 10.

12. A composition for producing D-tagatose, comprising the hexuronate C4-epimerase variant according to claim 1.

13. A method for preparing D-tagatose, comprising:
  epimerizing D-fructose by contacting D-fructose with the hexuronate C4-epimerase variant according to claim 1.

14. The method for preparing D-tagatose according to claim 13, wherein the epimerization is performed in the presence of a metal salt.

15. The method for preparing D-tagatose according to claim 13, further comprising:
   hydrolyzing sugar using an enzyme to obtain D-fructose or isomerizing glucose using an enzyme before the epimerization step.

16. A method for preparing D-tagatose, comprising:
   epimerizing D-fructose by contacting D-fructose with the transformant according to claim 11.

17. The method for preparing D-tagatose according to claim 16, wherein the epimerization is performed in the presence of a metal salt.

18. The method for preparing D-tagatose according to claim 16, further comprising:
   hydrolyzing sugar using an enzyme to obtain D-fructose or isomerizing glucose using an enzyme before the epimerization step.

19. A method for preparing D-tagatose, comprising:
   epimerizing D-fructose by contacting D-fructose with the composition for producing D-tagatose according to claim 12.

20. The method for preparing D-tagatose according to claim 19, wherein the epimerization is performed in the presence of a metal salt.

* * * * *

SEQUENCE LISTING

<160> NUMBER OF SEQ ID NOS: 4

<210> SEQ ID NO 1
<211> LENGTH: 481
<212> TYPE: PRT
<213> ORGANISM: Thermotoga neapolitana

<400> SEQUENCE: 1

```
Met Val Leu Lys Val Phe Lys Asp His Phe Gly Arg Gly Tyr Glu Val
1               5                   10                  15

Tyr Glu Lys Ser Tyr Arg Glu Lys Asp Ser Leu Ser Phe Phe Leu Thr
                20                  25                  30

Lys Gly Glu Glu Gly Lys Ile Leu Val Val Ala Gly Glu Lys Ala Pro
            35                  40                  45

Glu Gly Leu Ser Phe Phe Lys Lys Gln Arg Val Glu Gly Val Ser Phe
        50                  55                  60

Phe Phe Cys Glu Arg Asn His Glu Asn Leu Glu Val Leu Arg Lys Tyr
65                  70                  75                  80

Phe Pro Asp Leu Lys Pro Val Arg Ala Gly Leu Arg Ala Ser Phe Gly
                85                  90                  95

Thr Gly Asp Arg Leu Gly Ile Thr Thr Pro Ala His Val Arg Ala Leu
            100                 105                 110

Lys Asp Ser Gly Leu Phe Pro Ile Phe Ala Gln Gln Ser Val Arg Glu
        115                 120                 125

Asn Glu Arg Thr Gly Arg Thr Trp Arg Asp Val Leu Asp Asp Ala Thr
130                 135                 140

Trp Gly Val Phe Gln Glu Gly Tyr Ser Glu Gly Phe Gly Ala Asp Ala
145                 150                 155                 160

Asp His Val Lys Arg Pro Glu Asp Leu Val Ser Ala Ala Arg Glu Gly
                165                 170                 175

Phe Thr Met Phe Thr Ile Asp Pro Ser Asp His Val Arg Asn Leu Ser
            180                 185                 190

Lys Leu Ser Glu Arg Glu Lys Asn Glu Met Phe Glu Glu Ile Leu Lys
        195                 200                 205

Lys Glu Arg Ile Asp Arg Ile Tyr Leu Gly Lys Lys Tyr Thr Val Leu
210                 215                 220

Gly Glu Arg Leu Glu Phe Asp Glu Lys Asn Leu Arg Asp Ala Ala Leu
225                 230                 235                 240

Val Tyr Tyr Asp Ala Ile Ala His Val Asp Met Met Tyr Gln Ile Leu
                245                 250                 255

Lys Asp Glu Thr Pro Asp Phe Asp Phe Glu Val Ser Val Asp Glu Thr
            260                 265                 270

Glu Thr Pro Thr Ser Pro Leu Phe His Ile Phe Val Val Glu Glu Leu
        275                 280                 285

Arg Arg Arg Gly Val Glu Phe Thr Asn Leu Ala Leu Arg Phe Ile Gly
290                 295                 300

Glu Trp Glu Lys Gly Ile Asp Tyr Lys Gly Asp Leu Ala Gln Phe Glu
305                 310                 315                 320
```

```
Arg Glu Ile Lys Met His Ala Glu Ile Ala Arg Met Phe Glu Gly Tyr
                325                 330                 335

Lys Ile Ser Leu His Ser Gly Ser Asp Lys Phe Ser Val Tyr Pro Ala
                340                 345                 350

Phe Ala Ser Ala Thr Gly Gly Leu Phe His Val Lys Thr Ala Gly Thr
                355                 360                 365

Ser Tyr Leu Glu Ala Val Lys Val Ile Ser Met Val Asn Pro Glu Leu
            370                 375                 380

Phe Arg Glu Ile Tyr Arg Cys Ala Leu Asp His Phe Glu Glu Asp Arg
385                 390                 395                 400

Lys Ser Tyr His Ile Ser Ala Asp Leu Ser Lys Val Pro Glu Val Glu
                405                 410                 415

Lys Val Lys Asp Glu Asp Leu Pro Gly Leu Phe Glu Asp Ile Asn Val
                420                 425                 430

Arg Gln Leu Ile His Val Thr Tyr Gly Ser Val Leu Lys Asp Ala Ser
                435                 440                 445

Leu Lys Glu Arg Leu Phe Lys Thr Leu Glu Gln Asn Glu Glu Leu Phe
        450                 455                 460

Tyr Glu Thr Val Ala Lys His Ile Lys Arg His Val Asp Leu Leu Lys
465                 470                 475                 480

Gly

<210> SEQ ID NO 2
<211> LENGTH: 1446
<212> TYPE: DNA
<213> ORGANISM: Artificial Sequence
<220> FEATURE:
<223> OTHER INFORMATION: Nucleotide suquence of a wild type of
      hexuronate C4-epimerase

<400> SEQUENCE: 2
atggtcttga aagtgttcaa agatcacttt ggaaggggat acgaagttta cgaaaagtct      60
tatagagaaa aggattctct ctctttcttc ttgacaaagg gagaggaagg aaaaattctg     120
gtagtggctg agaaaaaggc acctgagggt ctgtcgtttt tcaaaaaaca gcgggtggag     180
ggtgtttcgt tcttttttct gtgagagaaat catgagaact tggaagttct cagaaaatac     240
tttccagatc tcaaaccagt tcgagcggga ttgagagcgt cttttggaac aggtgacaga     300
ctcggtatca ccacaccggc tcacgtgagg gcgttgaagg attcagggct ttttcccatc     360
tttgcgcagc agtcggtgag ggagaacgag agaacgggaa ggacctggag agatgtgctg     420
gacgatgcca catggggagt tttccaggag ggatacagtg agggattcgg agcagacgcc     480
gatcacgtga gcggccggaa ggatcttgtt tcggctgcaa gggaaggttt caccatgttc     540
acaatcgatc cttcggatca tgtgaggaat cttcaaaac tcagtgaaag agaaaagaac     600
gagatgttcg aggaaatact gaaaaaagag cgaatcgaca ggatctatct tgggaaaaaa     660
tacaccgtcc tcggtgaaag actggagttc gacgagaaaa atttgaggga tgctgctctg     720
gtgtactatg atgcgatcgc ccacgtggat atgatgtatc aaattttgaa agacgaaacc     780
ccggatttcg acttcgaagt gtcagttgac gaaacagaaa ctcccacgag tcctctcttc     840
cacattttcg ttgtggaaga actcagacga agaggtgtgg agttcaccaa tcttgccctg     900
agattcatcg cgaatgggaa aagggaata gattacaagg gggatcttgc acagttcgag     960
agagaaatca aaatgcacgc agaaatcgca aggatgttcg aaggatacaa atatcactc    1020 cactctggaa gcgacaaatt ttccgtgtat cctgctttg cttccgcgac aggaggcctt    1080
```

```
ttccacgtga agacagccgg aacgagttat cttgaggcgg tgaaggtcat atccatggtc    1140
aacccggagc tcttccggga gatctacagg tgtgctctcg atcactttga ggaagacaga    1200
aagtcctatc acatatctgc ggatctgtcg aaagttccgg aagtagagaa agtgaaagat    1260
gaagatcttc caggtctttt tgaagacatc aacgtgagac agttgatcca tgtcacctat    1320
ggctctgttc tgaaagatgc atctttgaaa gaacggctgt ttaagacgct tgaacaaaat    1380
gaggaactct tctacgagac cgtggcaaaa catataaaaa ggcacgtaga cctgttgaag    1440
gggtga                                                              1446
```

<210> SEQ ID NO 3
<211> LENGTH: 481
<212> TYPE: PRT
<213> ORGANISM: Artificial Sequence
<220> FEATURE:
<223> OTHER INFORMATION: A variant of hexuronate C4-epimerase

<400> SEQUENCE: 3

```
Met Val Leu Lys Val Phe Lys Asp His Phe Gly Arg Gly Tyr Glu Val
1               5                   10                  15

Tyr Glu Lys Ser Tyr Arg Glu Lys Asp Ser Leu Ser Phe Phe Leu Thr
            20                  25                  30

Lys Gly Glu Glu Gly Lys Ile Leu Val Val Ala Gly Glu Lys Ala Pro
        35                  40                  45

Glu Gly Leu Ser Phe Phe Lys Lys Gln Arg Val Glu Gly Val Ser Phe
    50                  55                  60

Phe Phe Cys Glu Arg Asn His Glu Asn Leu Glu Val Leu Arg Lys Tyr
65                  70                  75                  80

Phe Pro Asp Leu Lys Pro Val Arg Ala Gly Leu Arg Ala Ser Phe Gly
                85                  90                  95

Thr Gly Asp Arg Leu Gly Ile Thr Thr Pro Ala His Val Arg Ala Leu
            100                 105                 110

Lys Asp Ser Gly Leu Phe Pro Ile Phe Ala Gln Gln Asp Val Arg Glu
        115                 120                 125

Asn Glu Arg Thr Gly Arg Thr Trp Arg Asp Val Leu Asp Asp Ala Thr
    130                 135                 140

Trp Gly Val Phe Gln Glu Gly Tyr Ser Glu Gly Phe Gly Ala Asp Ala
145                 150                 155                 160

Asp His Val Lys Arg Pro Glu Asp Leu Val Ser Ala Ala Arg Glu Gly
                165                 170                 175

Phe Thr Met Phe Thr Ile Asp Pro Gln Asp His Val Arg Asn Leu Ser
            180                 185                 190

Lys Leu Ser Glu Arg Glu Lys Asn Glu Met Phe Glu Glu Ile Leu Lys
        195                 200                 205

Lys Glu Arg Ile Asp Arg Ile Tyr Leu Gly Lys Lys Tyr Thr Val Leu
    210                 215                 220

Gly Glu Arg Leu Glu Phe Asp Glu Lys Asn Leu Arg Asp Ala Ala Leu
225                 230                 235                 240

Val Tyr Tyr Asp Ala Ile Ala His Val Asp Met Met Tyr Gln Ile Leu
                245                 250                 255

Lys Asp Glu Thr Pro Asp Phe Asp Phe Glu Met Thr Val Asp Glu Asp
            260                 265                 270

Glu Thr Pro Thr Ser Pro Leu Phe His Ile Phe Val Val Glu Glu Leu
        275                 280                 285
```

```
Arg Arg Arg Gly Val Glu Phe Thr Asn Leu Ala Leu Arg Phe Ile Gly
290                 295                 300

Glu Met Glu Lys Gly Ile Asp Tyr Lys Gly Asp Leu Ala Gln Phe Glu
305                 310                 315                 320

Arg Glu Ile Lys Met His Ala Glu Ile Ala Arg Met Phe Glu Gly Tyr
                325                 330                 335

Lys Ile Ser Leu His Ser Gly Ser Asp Lys Phe Ser Val Tyr Pro Ala
                340                 345                 350

Phe Ala Ser Ala Thr Gly Gly Leu Phe His Val Lys Thr Ala Gly Thr
                355                 360                 365

Ser Tyr Leu Glu Ala Val Lys Val Ile Ser Met Val Asn Pro Glu Leu
370                 375                 380

Phe Val Glu Ile Tyr Arg Cys Ala Leu Asp His Phe Glu Asp Arg
385                 390                 395                 400

Lys Ser Thr His Ile Ser Ala Asp Leu Ser Lys Val Pro Glu Val Glu
                405                 410                 415

Lys Val Lys Asp Glu Asp Leu Pro Gly Leu Phe Glu Asp Ile Asn Val
                420                 425                 430

Arg Gln Leu Ile His Val Thr Tyr Gly Ser Val Leu Lys Asp Ala Ser
                435                 440                 445

Leu Lys Glu Arg Leu Phe Lys Thr Leu Glu Gln Asn Glu Glu Leu Phe
450                 455                 460

Tyr Glu Thr Val Ala Lys His Ile Lys Arg His Val Asp Leu Leu Lys
465                 470                 475                 480

Gly

<210> SEQ ID NO 4
<211> LENGTH: 1446
<212> TYPE: DNA
<213> ORGANISM: Artificial Sequence
<220> FEATURE:
<223> OTHER INFORMATION: Nucleotide sequence of a variant of hexuronate
      C4-epimerase

<400> SEQUENCE: 4
atggtcttga aagtgttcaa agatcacttt ggaaggggat acgaagttta cgaaaagtct      60
tatagagaaa aggattctct ctctttcttc ttgacaaagg gagaggaagg aaaaattctg     120
gtagtggctg gagaaaaggc acctgagggt ctgtcgtttt tcaaaaaaca gcgggtggag     180
ggtgtttcgt tcttttttctg tgagagaaat catgagaact ggaagttcct cagaaaatac     240
tttccagatc tcaaaccagt tcgagcggga ttgagagcgt cttttggaac aggtgacaga     300
ctcggtatca ccacaccggc tcacgtgagg gcgttgaagg attcagggct ttttcccatc     360
tttgcgcagc aggacgtgag ggagaacgag agaacgggaa ggacctggag agatgtgctg     420
gacgatgcca catggggagt tttccaggag ggatacagtg agggattcgg agcagacgcc     480
gatcacgtga gcggccgga ggatcttgtt tcggctgcaa gggaaggttt caccatgttc     540
acaatcgatc ctcaggatca tgtgaggaat cttctcaaaac tcagtgaaag agaaaagaac     600
gagatgttcg aggaaatact gaaaaaagag cgaatcgaca ggatctatct tgggaaaaaa     660
tacaccgtcc tcggtgaaag actggagttc gacgagaaaa atttgaggga tgctgctctg     720
gtgtactatg atgcgatcgc ccacgtggat atgatgtatc aaattttgaa agacgaaacc     780
ccggatttcg acttcgaaat gacagttgac gaagatgaaa ctcccacgag tcctctcttc     840
cacattttcg ttgtggaaga actcagacga agaggtgtgg agttcaccaa tcttgccctg     900
```

```
agattcatcg gcgaaatgga aaagggaata gattacaagg gggatcttgc acagttcgag      960
agagaaatca aaatgcacgc agaaatcgca aggatgttcg aaggatacaa aatatcactc     1020
cactctggaa gcgacaaatt ttccgtgtat cctgcttttg cttccgcgac aggaggcctt     1080
ttccacgtga agacagccgg aacgagttat cttgaggcgg tgaaggtcat atccatggtc     1140
aacccggagc tcttcgttga gatctacagg tgtgctctcg atcactttga ggaagacaga     1200
aagtccacac acatatctgc ggatctgtcg aaagttccgg aagtagagaa agtgaaagat     1260
gaagatcttc caggtctttt tgaagacatc aacgtgagac agttgatcca tgtcacctat     1320
ggctctgttc tgaaagatgc atctttgaaa gaacggctgt ttaagacgct tgaacaaaat     1380
gaggaactct tctacgagac cgtggcaaaa catataaaaa ggcacgtaga cctgttgaag     1440
gggtga                                                                1446
```